United States Patent
Pigamo et al.

(10) Patent No.: US 11,555,002 B2
(45) Date of Patent: *Jan. 17, 2023

(54) METHOD TO NEUTRALIZE AND REMOVE HF FROM A CRUDE STREAM CONTAINING HYDROCHLOROFLUOROOLEFIN

(71) Applicant: Arkema Inc., King of Prussia, PA (US)

(72) Inventors: Anne M. Pigamo, Francheville (FR); Jay F. Miller, Downingtown, PA (US); Emmanuel D. Boussaire, Decines Charpieu (FR); Kevin Hisler, Chaponnay (FR)

(73) Assignee: Arkema Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/293,645

(22) PCT Filed: Oct. 10, 2019

(86) PCT No.: PCT/US2019/055546
§ 371 (c)(1),
(2) Date: May 13, 2021

(87) PCT Pub. No.: WO2020/101824
PCT Pub. Date: May 22, 2020

(65) Prior Publication Data
US 2022/0009860 A1    Jan. 13, 2022

Related U.S. Application Data

(60) Provisional application No. 62/767,528, filed on Nov. 15, 2018.

(51) Int. Cl.
*C07C 17/395*  (2006.01)
*C07C 17/42*  (2006.01)

(52) U.S. Cl.
CPC ............ *C07C 17/395* (2013.01); *C07C 17/42* (2013.01)

(58) Field of Classification Search
CPC ..... C07C 17/395; C07C 17/383; C07C 17/42; C07C 21/18
See application file for complete search history.

(56) References Cited

U.S. PATENT DOCUMENTS 9,272,968 B2   3/2016  Kopkalli et al.
9,540,296 B2   1/2017  Chiu et al.
(Continued)

FOREIGN PATENT DOCUMENTS

WO   WO 2014/152325 A1   9/2014

*Primary Examiner* — Jafar F Parsa
(74) *Attorney, Agent, or Firm* — Steven D. Boyd

(57) ABSTRACT

Disclosed is a step in the purification process of hydrochlorofluoroolefin refrigerants that are made from processes wherein 1,1,3,3 tetrachloropropene (R1230za) or 1,1,1,3,3-pentachloropropane (R240fa) is reacted with HF in excess. The purification process employs a cold-temperature reaction with a base to remove the HF and any HCl. The process prevents an increase in unwanted organic side-products, particularly trifluoropropyne (TPS), and simultaneously does not reduce the amount of the desired hydrochlorofluoroolefin refrigerant produced. The process also can have an optional step whereby hydrochlorofluoroolefin refrigerant and other organics are removed from aqueous process stream or streams resulting from the reaction with the base. The organics removed can be recycled. This optional step advantageously can increase the yield of the desired refrigerant, while decreasing the environmental load of the plant, by purifying the resulting aqueous process streams.

15 Claims, 2 Drawing Sheets

(56) References Cited

U.S. PATENT DOCUMENTS

| | | |
|---|---|---|
| 11,286,223 B2 * | 3/2022 | Pigamo ................. C07C 17/383 |
| 2008/0051611 A1 | 2/2008 | Wang et al. |
| 2012/0059199 A1 | 3/2012 | Pokrovski et al. |
| 2012/0065437 A1 | 3/2012 | Merkel et al. |
| 2014/0275662 A1 | 9/2014 | Ball et al. |
| 2020/0407296 A1 | 12/2020 | Sharratt |

* cited by examiner

METHOD TO NEUTRALIZE AND REMOVE HF FROM A CRUDE STREAM CONTAINING HYDROCHLOROFLUOROOLEFIN

This present application is the national phase under 35 USC § 371 of prior PCT International Application Number PCT/US2019/055546 filed Oct. 10, 2019 which designated the United States of America and claimed priority to U.S. Provisional Patent Application Ser. No. 62/767,528 filed Nov. 15, 2018.

FIELD OF THE INVENTION

The invention relates to a step in the purification process of hydrochlorofluoroolefin or hydrochlorofluoroalkane refrigerants that are made from a process whereby a starting material is reacted with HF. When making such compounds in this way, there is a need to remove small amounts of HF and/or HCl from an organic-rich process stream that, in addition to the desired refrigerant, may also contain small but undesirable amounts of other organic products produced as side reactions during the synthesis reaction. The inventive process employs a cold-temperature reaction system utilizing ammonia or a basic salt of an alkali metal or alkaline earth metal (e.g., NaOH, KOH) with optional reducing agents such as bisulfite, sulfite or mixtures thereof, to remove the HF and HCl. Loss of the desired hydrochlorofluoroolefin or hydrochlorofluoroalkane product is reduced, while simultaneously minimizing increases in other unwanted products, particularly trifluoropropyne (TFP). The inventive process also comprises an optional step whereby the refrigerant is removed from the resulting aqueous process stream that is saturated with the refrigerant and the other organics produced as side reactions.

BACKGROUND OF THE INVENTION

There is a continuing pressure to produce more environmentally friendly versions of refrigerants, heat transfer fluids, foam blowing agents, solvents, etc. that not only have lower ozone depleting potential, but that also do not contribute to global warming. Chlorofluorocarbons (CFC) and hydrochlorofluorocarbons (HCFCs), widely used for these applications, are ozone depleting substances and are being phased out in accordance with guidelines of the Montreal Protocol. Hydrofluorocarbons (HFCs) are a leading replacement for CFCs and HCFCs in many applications; although they are safe for the ozone layer, they still generally possess high global warming potential and for that reason there is increasing need to minimize their use as well.

One class of compounds that has been identified to replace ozone depleting and high global warming substances are halogenated olefins, such as hydrofluoroolefins (HFO) and hydrochlorofluoroolefins (HCFO). The HFOs and HCFOs provide the low global warming potential and zero or near zero ozone depletion properties desired. An exemplary such HCFO is R1233zd-E, trans (E) 1-chloro-3,3,3, trifluoropropene.

A typical process for producing R1233zd-E is the reaction of 1,1,3,3 tetrachloropropene (R1230za) or 1,1,1,3,3 pentachloropropane (R240fa) with HF. An example of such a process is described in U.S. Pat. No. 9,061,958 which is incorporated by reference in its entirety herein for all purposes.

This invention pertains to not only R1233zd, but any HCFO or hydrochlorofluoroalkane with a normal boiling point greater than greater than 0° C., preferably greater than 10° C. and most preferably greater than 15° C. For example, all the isomers of R1233 such as R1233zd-E, R1233zd-Z and R1233xf, and others may be processed according to the processes disclosed herein.

The hydrofluorination reaction can be done in the gas or the liquid phase using any reactor known in the art, e.g., a tubular reactor, plug flow reactor, stirred tank reactor, or un-stirred tank reactor. The reaction may be catalyzed with a homogeneous or heterogeneous catalyst, or the reaction can be run uncatalyzed. The product of the reaction can be distilled, in either a distillation column or partial column such as a rectification column, to remove light products and recover heavier reactants and intermediates to recycle back to the reactor. The light products from the reactor will contain organics, HCl and HF that were either carried overhead in the distillation column by the normal operation of the column or taken overhead as part of an organic-HF azeotrope.

Generally, the next step is HCl removal by distillation. Trace amounts of HCl may remain in the bottom stream. The HCl stream is considered a product stream wherein the HCl may optionally be further purified and/or diluted with water for sale.

The bottoms stream is then sent to a separator to remove most of the HF from the organics. This separator may involve distillation, extraction, adsorption, or preferably decantation (i.e., the separator may be a decanter). When using a decanter, the HF-rich phase may contain between 20 and 40 wt % organics. This stream can optionally be sent to a distillation column to remove the organics, or organic-HF azeotropes. The HF is sent back to the reactor and the organic-rich stream is sent back to the decanter.

The organic-rich stream from the separator, i.e., the bottoms stream from a decanter, contains some HF, typically between 0.1 and 6 wt %. There is a need to remove the HF from this stream, which is a crude mixture of the desired refrigerant and small amounts of impurities such as undesired isomers, under and over-fluorinated side products as well as traces of HCl that is produced as a result of the reaction.

There are a number of possibilities to recover and purify the desired refrigerant and remove the remaining HF.

To remove HF from this crude refrigerant stream, many of the current processes pass the vaporized stream through an aqueous or aqueous-basic stream in an absorber tower. Typically, this processing is done with very volatile products to keep the temperature low enough to ensure no unwanted side reactions take place. The first step is to pass the crude stream through an aqueous absorber to remove most of the HF. Then the stream passes through an absorber with a basic or basic-reducing agent stream. The base in the aqueous stream reacts with HF forming a salt, which then flows with the aqueous stream and out the tails of the tower. The heads of the tower contain the HF-free refrigerant which then goes to one or more distillation towers for further purification. However, when processing crude R1233zd-E, this type of process cannot be used because the R1233zd-E and R1233zd-Z are not volatile enough to stay in the vapor phase unless high temperatures or vacuum are employed. Furthermore, when the crude R1233zd-E containing R1233zd-Z contacts the basic stream at high temperatures, undesired reactions occur. The high temperature can be reduced with vacuum, but vacuum is costly.

U.S. Pat. No. 9,221,732 teaches a method of separating crude R1233zd-E containing HF and HCl. The method comprises reducing the HCl level so that the mixture phase-separates. The upper layer contains most of the HF and the lower layer contains predominately R1233zd-E with low levels of HF and HCl. The HF and HCl are removed by washing the stream with an aqueous solution or an aqueous alkaline solution. There is no disclosure of further purification of the wet R1233zd-E, nor of efforts to minimize undesired products which result from washing the solution with base.

U.S. Pat. No. 9,272,968 discloses a method to suppress the formation of 3,3,3-trifluoropropyne (TFP), a toxic flammable material that can be formed due to reaction of R1233zd with the basic solution. The disclosed process comprises a method whereby the HF is removed with water in two separate washing steps and the resulting solution is then dried by way of a $H_2SO_4$ absorption system. In a second embodiment, the second water wash step is replaced with a washing step with a weak caustic solution (pH 7-pH 10). The resulting stream then can be dried with $H_2SO_4$. In another embodiment, rather than $H_2SO_4$, the water and trace HF are removed with a solid desiccant.

U.S. Pat. No. 9,540,296 discloses a process wherein a crude stream of R1233zd contains HCl in addition to a low level of HF. This stream is washed with an aqueous or basic solution, resulting in a wet vapor which is condensed. The resulting liquid mixture, containing HCFO-1233zd, other organics, and water, is allowed to settle, and thereafter, the lighter water layer is decanted off from the top of the mixture. The heavier HCFO-1233zd layer is then withdrawn from the bottom of the decanter to a desiccant dryer (e.g., molecular sieve, activated alumina, silica gel, and the like) to further reduce the level of residual soluble moisture from the HCFO-1233zd to about 80 ppm or less. The disclosure does not describe a method whereby the levels of the undesired organics or TFP can be controlled by the method of effecting the washing step.

U.S. Patent Application Publ. No. 2013/0158305 discloses a method for removing moisture from fluorine-containing compounds. The method comprising bringing a fluorine-containing compound contaminated with moisture into contact with an aqueous solution containing a metal salt. The disclosed method can continuously and efficiently remove moisture from various fluorine-containing compounds, such as hydrofluoroolefins. The disclosure does not discuss a particular method to remove low levels of HF from the crude refrigerant stream.

U.S. Patent Application Publ. No. 2017/0081265 discloses separation processes that use azeotropic or azeotropic-like compositions of 1-chloro-3,3,3-trifluoropropene (HCFO-1233zd). The separation processes utilize the azeotropic or azeotropic-like properties of the compositions with various combinations of separation techniques (e.g., distillation and decanting) to purify 1-chloro-3,3,3-trifluoropropene.

There is thus a need for processes that can remove the HF from a process stream comprising crude R1233zd-E with undesired organics, without decreasing the amount of the desired R1233zd-E or creating 3,3,3-trifluoropropyne (TFP) and other undesirable organics. Additionally, there remains a need to economically and ecologically remove traces of refrigerant from the effluent water.

SUMMARY OF THE INVENTION

We have unexpectedly found that mixing an R1233zdE crude stream, which typically contains 0.1-6.0 wt % HF, with a caustic stream at a pH greater than 10 at temperatures less than 50° C. and preferably less than 40° C., and most preferably less than 20° C., converts the HF and HCl to salts yet does not significantly alter the composition of the crude R1233zd-E organic constituents markedly. The stream is then split into an organic phase containing crude R1233zd-E and an aqueous phase containing the salts of HF and unreacted basic species. The crude R1233zd-E may be dried by conventional means, e.g., molecular sieves, and then distilled to remove light and heavy by-products in order to produce purified R1233zd-E.

The aqueous stream may optionally be sent to a stripper to remove the trace amounts of crude R1233zd-E. The stripping agent may be steam, air, nitrogen or the like; preferably, it is steam. The overheads from the stripping column phase separate into two liquid phases, a crude R1233zd-E phase and an aqueous phase. The crude R1233zd-E stream is sent for purification to produce purified R1233zd-E. The aqueous phase is sent back into the stripping column or sent to waste treatment. In this way the aqueous stream has only trace amounts of organics and can be disposed of easily.

Within this specification, embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

In some embodiments, the invention herein can be construed as excluding any element or process step that does not materially affect the basic and novel characteristics of the method. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

Various non-limiting aspects of the invention may be summarized as follows:

Aspect 1: A method for removing an acid, wherein the acid comprises at least one of HF or HCl, from a crude HCFO stream, wherein the method comprises the step of: b) contacting the crude HFCO stream with an aqueous base stream, wherein step b) takes place at a reaction temperature; whereby the base reacts with the at least one of HF or HCl forming a salt, whereby the removal of at least one of HF or HCl is accomplished by removal of the salt and wherein step b) produces a reduced acid crude HFCO stream comprising less than 3000 µmol/mol of trifluoropropyne and a basic aqueous trace crude HFCO stream comprising the salt, wherein the reaction temperature is less than 50° C.

Aspect 2: The method according to claim 1, further comprising a step a) wherein step a) is performed before step b) and step a) comprises a step of contacting the crude HFCO stream with a water stream whereby the water stream dissolves at least a portion of the at least one of HF or HCl, whereby partial removal of at least one of HF or HCl from the crude HFCO stream is accomplished, wherein step a) produces an aqueous HF/HCl/trace crude HFCO stream and a partially reduced acid crude HFCO stream and wherein the partially reduced acid crude HFCO stream is fed to step b) as the crude HCFO stream and wherein step a) takes place at a washing temperature.

Aspect 3: The method according to claim 1 or claim 2, wherein the method further comprises a step c), wherein step c) is performed after step b), and wherein the step c) comprises a step of removing trace crude HFCO from the basic aqueous trace crude HFCO stream emerging from step b).

Aspect 4: The method according to claim 3, wherein the step c) comprises stripping using a stripping agent and wherein the stripping agent is selected from the group consisting of air, nitrogen, and steam.

Aspect 5: The method according to claim 4 wherein the stripping agent comprises steam.

Aspect 6: The method according to claim 2, wherein the method further comprises a step d) wherein step d) is performed after step b) and wherein step d) comprises i) combining the basic aqueous trace crude HFCO stream emerging from step b) with the aqueous HF/HCl/trace crude HFCO stream emerging from step a) to produce a combined aqueous trace crude HFCO stream and ii) removing trace crude HFCO from the combined aqueous trace crude HFCO stream.

Aspect 7: The method according to claim 6, wherein ii) comprises stripping using a stripping agent and wherein the stripping agent is selected from the group consisting of air, nitrogen and steam.

Aspect 8: The method according to claim 7, wherein the stripping agent comprises steam.

Aspect 9: The method according to any of claims 1-8, wherein the HCFO is a monochloro-trifluoropropylene.

Aspect 10: The method according to any of claims 1-8, wherein the HCFO is selected from the group consisting of 1,1,1-trifluoro-3-chloropropene and 1,1,1-trifluoro-2-chloropropene.

Aspect 11: The method according to any of claims 1-8, wherein the HCFO is trans-1,1,1-trifluoro-3-chloropropene.

Aspect 12: The method according to any of claims 1-11, wherein the aqueous base is selected from the group consisting of aqueous potassium hydroxide and aqueous sodium hydroxide.

Aspect 13: The method according to any of claims 1-12, wherein the aqueous base is an aqueous solution comprised of 1 to 25% by weight potassium hydroxide.

Aspect 14: The method according to any of claims 1-13, wherein the aqueous base has a pH of at least 13.5.

Aspect 15: The method according to any of claims 1-14, wherein the reaction temperature is less than 30° C.

DETAILED DESCRIPTION OF THE INVENTION

Figure 1:
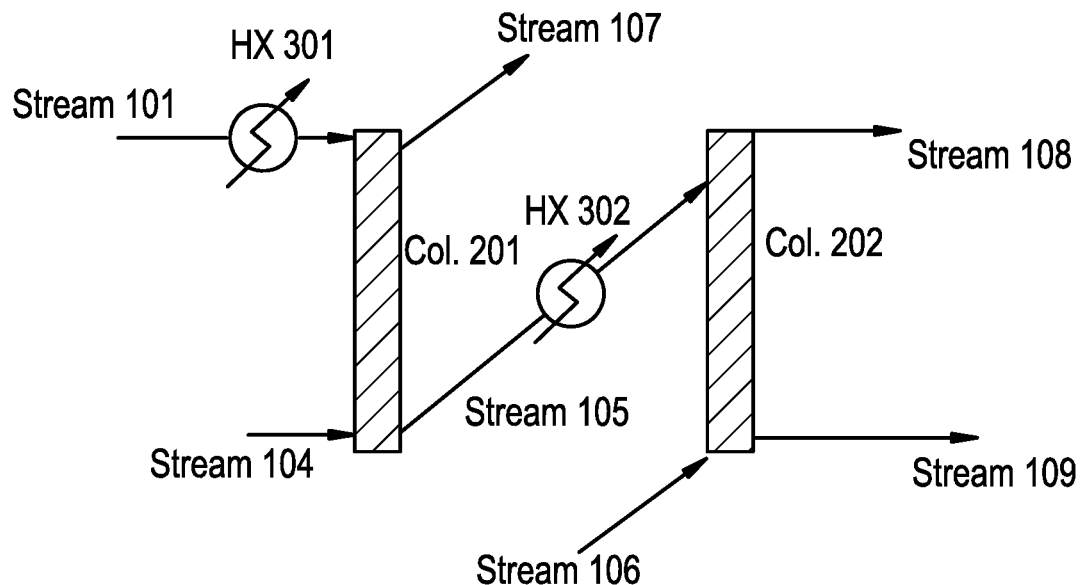
FIG. 1 shows an embodiment of the process according to the invention.

The nomenclature used to refer to certain streams or compounds (including refrigerants) discussed herein is as follows:

"R1233zd-E crude stream" means a stream containing mostly R1233zd-E, but also named and unnamed contaminants that has not been fully purified and does not meet the specifications for a pure product. The "R1233zd-E crude stream" may also be referred to as "R1233zd" or "1233zd". All of these recitations refer to a mixture comprising mostly the desired E isomer, but which is contaminated with the unwanted Z isomer and possible other side products.

R1233zd-E: trans-1,1,1-trifluoro-3-chloropropene
R1233zd-Z: cis-1,1,1-trifluoro-3-chloropropene
TFP: 3,3,3-trifluoro-1-propyne
R1234ze-E: trans-1,3,3,3-tetrafluoropropene
R1243zf: 3,3,3-trifluoropropene
R245fa: 1,1,1,3,3-pentafluoropropane
R1234ze-Z: trans-1,3,3,3-tetrafluoropropene
R243: all isomers of trifluorodichloropropane
R1223: all isomers of dichlorotrifluoropropylene
R1230za: 1,1,3,3-tetrachloropropene
R240fa: 1,1,1,3,3-pentachloropropane It should be understood that while the examples disclosed herein describe the exemplary purification of crude R1233zd-E, other halogenated propene compounds or hydrochlorofluoroalkanes are likewise suitable to be processed in the same way. Non-limiting examples of compounds that can be purified using the inventive process are: monochloro-trifluoropropenes such as trans-1,1,1-trifluoro-3-chloropropene; cis-1,1,1-trifluoro-3-chloropropene; 1,1,1-trifluoro-chloropropene.

When the refrigerant R1233zd-E is produced, one possible production route is to convert either R240fa or R1230za into R1233zd-E by a reaction with HF. The liberated HCl is removed and the resulting stream is sent to a decanter. The decanter operation is described in U.S. Pat. No. 8,735,636, the disclosure of which is incorporated herein in its entirety for all purposes. The top HF-rich phase from the decanter is sent directly, or optionally through an azeotrope column, back to the reactor that produces the R1233zd-E to recycle the excess HF. The bottom organic-rich phase from the decanter, containing mostly crude R1233zd-E, with about 0.1-6.0 wt % HF, is sent for further purification.

As discussed above, in order to purify crude R1233zd-E it is necessary to remove the HF and residual HCl. This is best done by reacting with a base and has been discussed in U.S. Pat. No. 9,061,958, the disclosure of which is incorporated herein in its entirety for all purposes. U.S. Pat. No. 9,061,958 mentions the removal of HF from R1233zd solutions by "water, aqueous NaOH, aqueous KOH and mixtures thereof."

When performing this neutralization reaction using a base under conditions that allow 1233zd-E (19° C. boiling point at 1.01325 MPa) and also optionally species such as 1233zd-Z to remain in the gas phase (38° C. boiling point at 1.01325 MPa), a portion of the R1233zd is converted into unwanted species. The unwanted species are both a yield loss and require more cost for their removal. Furthermore, when the neutralization reaction with the base is performed at 50° C., the concentration of trifluoropropyne (TFP) increases to the level of detectability. Production of TFP, even at extremely low levels, is a serious problem because it has potential high toxicity and is a flammable product. Additionally, the levels of some of the other undesirable side products of the reaction also increase at this temperature.

Conversely, the neutralization reactions can be done under temperatures less than 50° C. and preferably less than 45° C. or less than 40° C. or 35° C. or 30° C. Surprisingly, when carrying out the neutralization reactions at these lower temperatures, the amount of TFP by-product was reduced, but the removal of the HF and HCl was still effective.

The following description uses the block diagram in FIG. 1. The crude R1233zd-E stream, typically containing between 0.2 weight % and 6 weight % HF and possibly some HCl, enters the purification train in stream 101. Heat exchanger 301 serves to control the temperature of stream 101, including a phase change from vapor to liquid or vice versa, if necessary. In this example, stream 101 is assumed to be liquid when it exits heat exchanger 301, although a person having skill in the art can appreciate that stream 101 could be a vapor; this alternate embodiment will be addressed below.

FIG. 1 shows the crude R1233zd-E stream 101 which contains from 0.2 to 6 wt % HF and/or HCl. The temperature of stream 101 and the amount of HF in stream 101 depends on the previous steps. The temperature of stream 101 can range from −60° C. to 50° C. and stream 101 is liquid, as noted above. Stream 101 is taken to an optional water-absorber column 201, where water, stream 104, is employed to remove >90% of the HF and HCl from stream 101. Column 201 is thus operated as a liquid-liquid absorber column to remove much of the HF and/or HCl. The water, containing the removed HF and/or HCl exits column 201 as stream 107. The organic stream, washed crude R1233zd-E, exits this water-absorber step from column 201 as stream 105. At this point, the stream 105 still comprises small but unacceptable quantities of HF and/or HCl.

Stream 105 is next cooled in heat exchanger 302 to a temperature less than 50° C., and preferably less than 45° C. or less than 40° C. or less than 35° C. or less than 30° C. Exiting the heat exchanger 302, stream 105 is then taken to a second column, reactor-absorber column 202, in which an aqueous base stream, stream 106, is contacted with the cooled organic stream 105. Non-limiting examples of caustic (base) stream 106 comprise 5-10 weight percent aqueous solutions of bases such as NaOH, KOH, or ammonia. The base stream 106 may further comprise reducing agents, for example, but not limited to bisulfite, sulfites and mixtures thereof. The pH of stream 106 is preferably at least 10, or higher, such as at least 11 or at least 12 or at least 13 or at least 13.5 or at least 14. Stream 106 is advantageously lower than 50° C. or lower than 45° C. or lower than 40° C. or lower than 35° C. or lower than 30° C. Stream 109 emerges from from the reactor-separator column 202, which utilizes the basic stream 106 to remove HF and any HCl from stream 105. Stream 109 is therefore HCFO R1233zd-E which is essentially free of the acids HF and HCl, while stream 108, the emerging from from reactor-separator column 202 is an aqueous basic stream containing salts of HF and HCl that were removed from stream 105.

Figure 3:
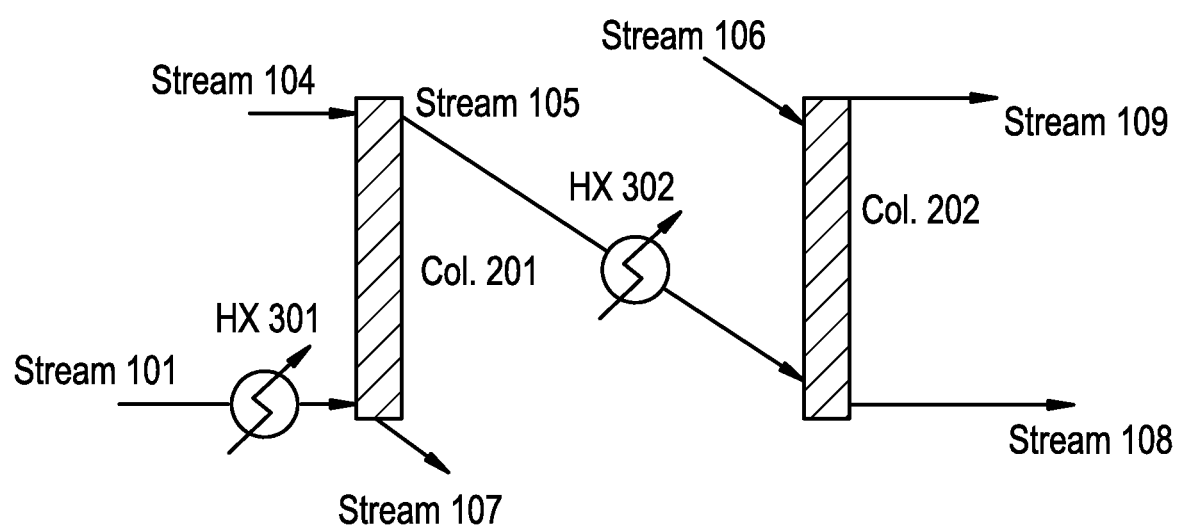
FIG. 3 shows a second embodiment of the invention.

In a second, alternative embodiment, water-absorber column 201 can be run as a vapor-liquid absorber as shown in FIG. 3. In this embodiment, the stream 101 exiting heat exchanger 301 is a vapor, and the column 201 is thus operated as a vapor-liquid absorber. Stream 101 as it exits from heat exchanger 301 would be fed to the bottom of column 201 and the water, stream 104, would be fed to the top of column 201. Stream 105 as it exits column 201 would then be a vapor, and heat exchanger 302 would cool stream 105 to a temperature less than 50° C., and preferably less than 45° C. or less than 40° C. or less than 35° C. or less than 30° C. Stream 105 at this point still contains a reduced but still unacceptable level of HF and possibly HCl. The operation of reactor-separator column 202 in this second embodiment, like the first embodiment shown in FIG. 1, serves to remove the remaining HF and HCl from stream 105.

Like the first embodiment, the aqueous basic stream 106 in this second embodiment is contacted with stream 105 in column 202 as shown in FIG. 3. The basic stream 106 thus removes HF and any HCl from stream 105. Stream 109 which emerges from column 202 is therefore HCFO R1233zd-E which is essentially free of the acids HF and HCl, while stream 108, emerging from reactor-separator column 202 is an aqueous basic stream containing salts of HF and HCl that were removed from stream 105.

Furthermore, there may be no water absorber column 201, since this step is optional, or there may be one or two or more water absorption columns 201. There is at least one and there may be more than one reactor-separator columns 202 utilizing a stream of an aqueous base, such as NaOH, KOH, or other base such as ammonia, either alone or in combination with a reducing agent such as bisulfite, sulfite or mixtures thereof, to remove the HF or HCl from stream 105. If optional water-absorber column 201 is not used, the stream 101 is fed directly to column 202 as described above. If stream 101 is a liquid the operation of column 202 is as shown in FIG. 1 and if stream 101 is a vapor, the operation of column 202 is as shown in FIG. 3.

At all times heat exchangers are employed to ensure the organic R1233zd crude stream remains cool, i.e., with a temperature rise of no more than 10° C., such that TFP is not formed and R1233zd-E is not lost.

The reactor-separator column 202 may be trayed or filled with either random or structured packing. The organic rich phase, stream 109, will contain a small amount of water which may be removed by molecular sieves, e.g., zeolite 3A. The adsorption by the molecular sieves may be accomplished in the liquid or the vapor phase. The organic stream 109 after this drying step is then sent to downstream processing to remove lights and heavies (i.e. unwanted organics) to produce purified R1233zd-E that meets all specifications.

The aqueous streams, stream 107 and 108, from the columns 201 and 202, respectively, typically contain about 450-500 ppm organics. These organics comprise HFCO. These streams 107 and 108 can be sent to the wastewater purification section of the plant or they can have the organics removed for recycle (which would increase the yield of the desired HFCO) and to reduce the environmental load of the plant.

Figure 2:
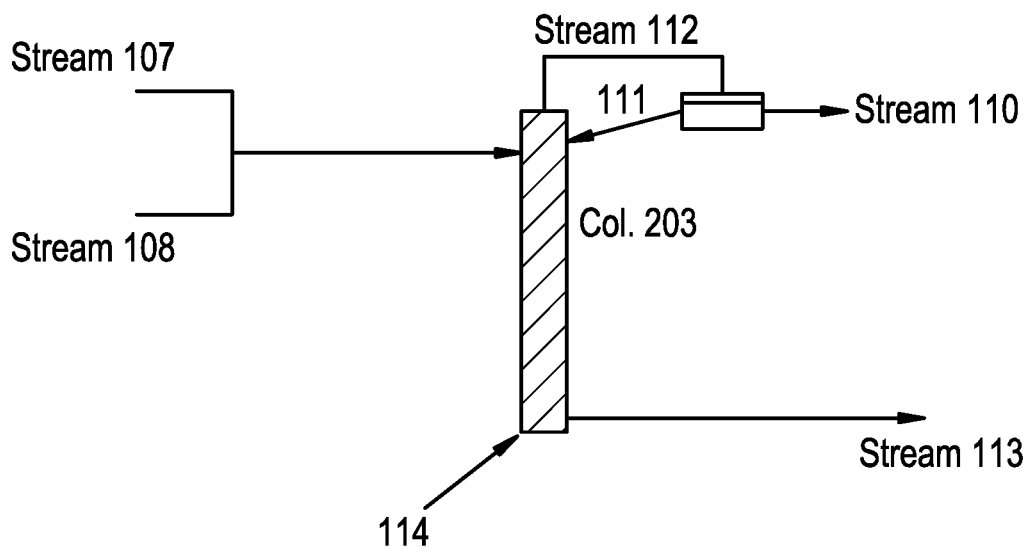
FIG. 2 shows an additional step in the process according to the invention.

A preferred way to remove the organics from the aqueous streams 107 and 108 is to employ a stripping column 203, shown in FIG. 2. The stripping agent, stream 114 can be steam, air, nitrogen or the like, with steam being preferred. The resulting aqueous stream, stream 113, is essentially free of organics and can be disposed of in a typical fashion. The overheads from the column 203 containing the organics, stream 112, are cooled to approximately 10° C. such that the stream 112 is mostly liquid, which will cause the stream to phase split into an organic rich stream 110, which is free of HF and free of any HCl that may have been in the crude 1233zdE, and an aqueous rich stream 111. The aqueous stream, 111, can be sent back, refluxed, into the stripping column 203 such that the water exiting the bottom of column 203 as stream 113 is essentially organic-free.

EXAMPLES

All the following examples were run by feeding crude R1233zd as a gas into the bottom of a 0.5 L temperature-controlled glass reactor at atmospheric pressure. The caustic solution was recirculated from the bottom of the reactor to the top of a column filled with glass packing. The crude R1233zd vapor bubbled through the caustic solution in the reactor and then passed counter currently through the column. The effluent gas, comprising the R1233zd, was dried with calcium chloride and analyzed by gas chromatography before and after scrubbing. Different types of caustic (i.e., KOH or NaOH) in solution were used at various concentrations and different temperatures were employed as well to determine the effect of temperature on the amount of TFP produced during the step of contacting the crude R1233zd with the caustic solution.

Example 1a: (Comparative)

In this Example, 5 weight % (0.9M) KOH solution, with a pH=13.95, at 50° C. The R1233zd was fed into the reactor at 7.5 g/hr and the KOH solution was recirculated at 185 mL/min.

When crude R1233zd was absorbed with 5% KOH solution at 50° C., significant amounts of TFP may be produced as shown in the experimental results presented in Table 1. The R1233zd-Z concentration was reduced from 2.4 mol % to 1.5 mol % and the TFP concentration increased from 0 to 8276 µmol/mol. The amount of the 1233zd-E isomer is essentially unchanged.

TABLE 1

Scrubbing of 1233zd solution with 5 weight % KOH at 50° C. Note that the concentrations of the TFP, R1233zd E and R1233zd Z are molar concentration.

| Example 1a (comparative) 50° C. | TFP (µmol/mol) | R1233zd E (percent molar) | R1233zd Z (percent molar) |
|---|---|---|---|
| Average before scrubbing | None detected | 95.74% | 2.44% |
| Average after scrubbing | 8276 | 95.89% | 1.53% |

Example 1b: (Invention)

Example 1b is the same as Example 1a (above) except that the reactor was controlled to 30° C. The feed rate of the crude R1233zd was 6.2 g/hr and the 5 weight % KOH solution was recirculated at 185 mL/min. The results are shown in Table 2 below. These results demonstrate that when operating at the lower temperature of 30° C., the amount of TFP formed is greatly reduced compared to the amount that was formed when the reactor was at 50° C., as shown in Table 2.

TABLE 2

Scrubbing of 1233zd solution, with 5 weight % KOH at 30° C. Note that the concentrations of TFP, R1233zd E and R1233zd Z are in molar concentration.

| Example 1b (invention) 30° C. | TFP (µmol/mol) | R1233zd E (percent molar) | R1233zd Z (percent molar) |
|---|---|---|---|
| Average before scrubbing | None detected | 95.74% | 2.39% |
| Average after scrubbing | 2709 ppm | 95.73% | 2.14% |

When the scrubbing is performed at 30° C., the concentration of TFP is greatly reduced from 8276 µmol/mol to about 2709 µmol/mol.

Example 2a: (Comparative)

In this example, 5 weight % NaOH, pH=14 at 50° C. is used. The feed rate of the crude R1233zd was 6.2 g/hr and the NaOH solution was recirculated at 185 mL/min. The 1233zd-Z concentration was reduced from 2.5 molar % to 1.6 molar % and the TFP increased from 0 to 7194 ppm molar.

Therefore, it is clear that when crude R1233zd was treated with 5 weight % NaOH solution at 50° C., undesirable amounts of TFP were produced as shown in the experimental results which are presented in Table 3. The amount of 1233zd-E isomer is essentially unchanged.

TABLE 3

Scrubbing of 1233zd solution with 5% NaOH at 50° C. Note that the concentrations of TFP, R1233zd E and R1233zd Z are in molar concentration.

| Example 2a (comparative) 50° C. | TFP (µmol/mol) | R1233zd E (percent molar) | R1233zd Z (percent molar) |
|---|---|---|---|
| Average before scrubbing | None detected | 95.69% | 2.51% |
| Average after scrubbing | 7194 ppm | 95.99% | 1.57% |

Example 2b (Invention)

Example 2b is the same as Example 2a (above) except that the reactor was controlled to 30° C. The feed rate of the crude R1233zd was 4.8 g/hr, and the NaOH solution was recirculated at 185 mL/min. At this lower temperature of 30° C., the amount of TFP formed was significantly reduced as compared to the amount formed at a scrubbing temperature of 50° C., as shown in Table 4.

TABLE 4

Scrubbing of 1233zd solution with 5 weight % NaOH at 30° C. Note the concentrations of TFP, R1233zd E and R1233zd Z are molar concentration.

| Example 2b (invention) 30° C. | TFP (µmol/mol) | R1233zd E (percent molar) | R1233zd Z (percent molar) |
|---|---|---|---|
| Average before scrubbing | None detected | 95.74% | 2.46% |
| Average after scrubbing | 2411 | 95.76% | 2.23% |

When the scrubbing is performed at 30° C., the concentration of TFP that is produced is greatly reduced from 7194 µmol/mol to about 2411 µmol/mol.

In some embodiments, the invention herein can be construed as excluding any element or process step that does not materially affect the basic and novel characteristics of the method. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

What is claimed is:
1. A method for removing an acid selected from the group consisting of HCl, HF and mixtures thereof, from a crude

HCFO stream, wherein the method comprises the step of: b) contacting the crude HFCO stream with an aqueous base stream at a pH above about 10 and at a temperature less than 50° C. whereby the base reacts with the acid forming a salt, whereby the removal of the acid is accomplished by removal of the salt to produces a reduced acid crude HFCO stream comprising less than 3000 μmol/mol of trifluoropropyne and a basic aqueous trace crude HFCO stream comprising the salt.

2. The method according to claim 1, further comprising a step a) wherein step a) is performed before step b) and step a) comprises contacting the crude HFCO stream with a water stream whereby the water stream dissolves at least a portion of the acid whereby partial removal of the acid from the crude HFCO stream is accomplished to produce an aqueous acid/trace crude HFCO stream and a partially reduced acid crude HFCO stream and wherein the partially reduced acid crude HFCO stream is fed to step b) as the crude HCFO stream and wherein step a) takes place at a washing temperature.

3. The method according to claim 1, wherein the method further comprises a step c), wherein step c) is performed after step b), and wherein the step c) comprises a step of removing trace crude HFCO from the basic aqueous trace crude HFCO stream emerging from step b).

4. The method according to claim 3, wherein the step c) comprises stripping using a stripping agent and wherein the stripping agent is selected from the group consisting of air, nitrogen, and steam.

5. The method according to claim 4 wherein the stripping agent comprises steam.

6. The method according to claim 2, wherein the method further comprises a step d) wherein step d) is performed after step b) and wherein step d) comprises i) combining the basic aqueous trace crude HFCO stream emerging from step b) with the aqueous acid/trace crude HFCO stream emerging from step a) to produce a combined aqueous trace crude HFCO stream and ii) removing trace crude HFCO from the combined aqueous trace crude HFCO stream.

7. The method according to claim 6, wherein ii) comprises stripping using a stripping agent and wherein the stripping agent is selected from the group consisting of air, nitrogen and steam.

8. The method according to claim 7, wherein the stripping agent comprises steam.

9. The method according to claim 1, wherein the HCFO is a monochloro-trifluoropropylene.

10. The method according to claim 1, wherein the HCFO is selected from the group consisting of 1,1,1-trifluoro-3-chloropropene and 1,1,1-trifluoro-2-chloropropene.

11. The method according to claim 1, wherein the HCFO is trans-1,1,1-trifluoro-3-chloropropene.

12. The method according to claim 1, wherein the aqueous base is selected from the group consisting of aqueous potassium hydroxide and aqueous sodium hydroxide.

13. The method according to claim 1, wherein the aqueous base is an aqueous solution comprised of 1 to 25% by weight potassium hydroxide.

14. The method according to claim 1, wherein the aqueous base has a pH of at least 13.5.

15. The method according to claim 1, wherein the reaction temperature is less than 30° C.

* * * * *